United States Patent

Buerstinghaus et al.

[11] Patent Number: 4,760,056
[45] Date of Patent: Jul. 26, 1988

[54] OXIMINOPHOSPHORIC ACID DERIVATIVES, AND THEIR USE FOR CONTROLLING PESTS

[75] Inventors: Rainer Buerstinghaus, Heidelberg; Franz Merger, Frankenthal; Rudolf Kropp, Limburgerhof; Karl Kiehs, Lampertheim; Heinrich Adolphi, Limburgerhof, all of Fed. Rep. of Germany

[73] Assignee: BASF Aktiengesellschaft, Fed. Rep. of Germany

[21] Appl. No.: 854,919

[22] Filed: Apr. 23, 1986

[30] Foreign Application Priority Data

Apr. 25, 1985 [DE] Fed. Rep. of Germany ....... 3514922
May 15, 1985 [DE] Fed. Rep. of Germany ....... 3517478
Aug. 9, 1985 [DE] Fed. Rep. of Germany ....... 3528599

[51] Int. Cl.$^4$ .................. A01N 57/02; C07F 9/165; C07F 9/40
[52] U.S. Cl. ..................... 514/114; 558/167
[58] Field of Search ................ 558/167; 514/114

[56] References Cited

U.S. PATENT DOCUMENTS

3,639,537 2/1972 Kaufman .................. 558/167
3,911,055 10/1975 Lorenz et al. .............. 558/167

Primary Examiner—Anton H. Sutto
Attorney, Agent, or Firm—Keil & Weinkauf

[57] ABSTRACT

Oximinophosphoric acid derivatives of the formula

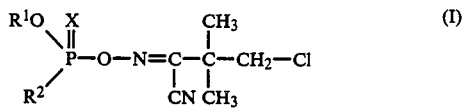

where $R^1$ is a straight-chain or branched alkyl of not more than 4 carbon atoms, $R^2$ is a straight-chain or branched alkoxy or alkylthio group of not more than 4 carbon atoms, straight-chain or branched alkyl of not more than 3 carbon atoms, phenyl, amino or a straight-chain or branched alkylamino or dialkylamino radical, where alkyl in each case is of not more than 4 carbon atoms, and X is oxygen or sulfur, a process for the manufacture of these oximinophosphoric acid derivatives, and their use for controlling pests.

7 Claims, No Drawings

OXIMINOPHOSPHORIC ACID DERIVATIVES, AND THEIR USE FOR CONTROLLING PESTS

The present invention relates to oximinophosphoric acid derivatives, a process for their preparation, pesticides which contain these phosphoric acid derivatives as active ingredients, and a method for controlling pests with these active ingredients.

Oximinophosphoric acid derivatives are disclosed in German Published Applications DAS Nos. 1,052,981 and 1,238,902 and German Laid-Open Applications DOS Nos. 2,304,848, 2,952,739, 3,135,182 and 3,302,969. They are useful for controlling insects and arachnids. However, their action is not always completely satisfactory, especially in low concentration.

We have found that oximinophosphoric acid derivatives of the formula I

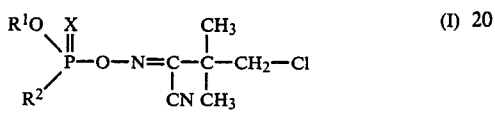

where $R^1$ is straight-chain or branched alkyl of not more than 4 carbon atoms, $R^2$ is a straight-chain or branched alkoxy or alkylthio group of not more than 4 carbon atoms, straight-chain or branched alkyl or not more than 3 carbon atoms, phenyl, amino or a straight-chain or branched alkylamino or dialkylamino radical, where alkyl in each case is of not more than 4 carbon atoms, and X is oxygen or sulfur, possess very good insecticidal, acaricidal and nematicidal activity and are superior to known active ingredients of similar structure or identical direction of action.

The oximinophosphoric acid derivatives of the formula I can be obtained by reacting an appropriate α-oximinonitrile with an appropriate (thiono)(thiol)phosphoric (phosphonic) ester (amide) halide:

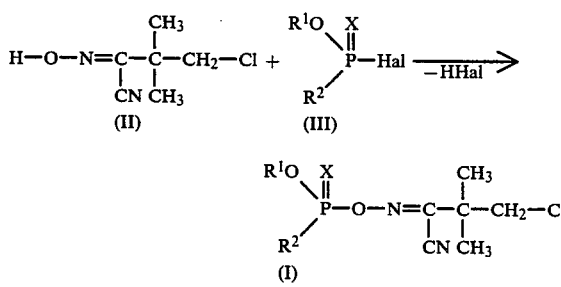

For economic reasons, hal(ogen) is preferably chlorine.

The reaction is advantageously carried out in a solvent or diluent, examples of suitable ones being aliphatic and aromatic hydrocarbons and aliphatic and aromatic chlorohydrocarbons, such as petroleum ether, benzene, toluene, xylene, gasolene, dichloromethane, chloroform, tetrachloromethane, 1,2-dichloroethane or chlorobenzene, ethers, such as diethyl ether, di-n-butyl ether, methyl tert-butyl ether, tetrahydrofuran or dioxane, ketones, e.g. acetone, methyl ethyl ketone or methyl isopropyl ketone, and nitriles such as acetonitrile or propionitrile. Mixtures of these substances may also be used as solvents or diluents.

Suitable acid acceptors are the basic agents conventionally used in the phosphorylation of hydroxy compounds. Alkali metal carbonates or alcoholates, such as sodium carbonate, potassium carbonate, sodium methylate, potassium methylate, sodium ethylate and potassium ethylate, and aliphatic, aromatic and heterocyclic amines, e.g. triethylamine, dimethylamine, piperidine, dimethylaniline, dimethylbenzylamine and pyridine, are particularly suitable. In some cases, it is advantageous to use an alkyl-lithium compound, e.g. n-butyllithium, or an alkali metal hydride, e.g. sodium hydride.

Instead of adding an acid acceptor, a salt of the α-oximinonitrile (II), for example an alkali metal, alkaline earth metal or ammonium salt, can be prepared before the reaction, and this salt reacted.

The starting materials are usually employed in stoichiometric amounts. In specific cases, an excess of one or other of the starting materials may be advantageous.

The reaction usually takes place at an adequate rate at above room temperature. In general, a temperature of 120° C. need not be exceeded. Since in some cases the reaction takes place with evolution of heat, it may be advantageous to provide a means of cooling.

The novel active ingredient is obtained from the reaction mixture in a conventional manner, for example by the addition of water, separation of the phases and distillation and/or column chromatography.

The α-oximinonitriles of the formula (II) which are used as starting materials for the preparation of compounds of the formula (I) are novel substances. However, they may be prepared in a conventional manner (German Published Application DAS No. 1,567,142), by chlorination of 2-methyl-2-(chloromethyl)-propionaldoxime (IV) followed by reaction with sodium cyanide or potassium cyanide, according to the following equation:

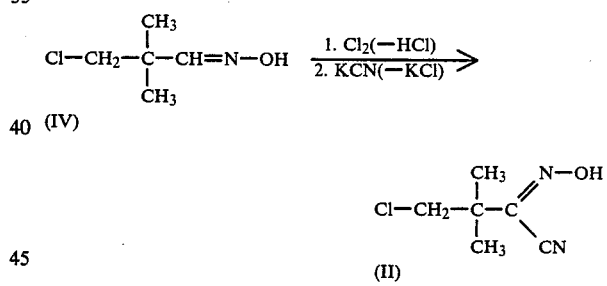

Oximes of the formula IV are obtained by reacting chloropivalaldehyde (V) with hydroxylamine hydrochloride according to the following equation:

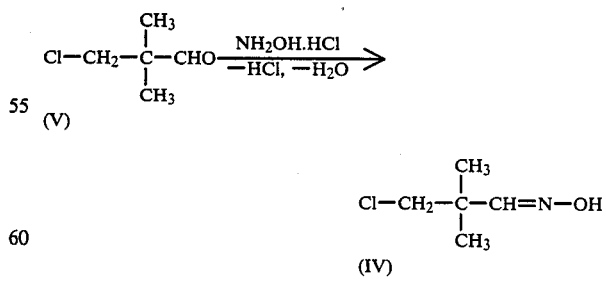

Chloropivalaldehyde is known from the literature (cf. J. Org. Chem. 43 (1978) 1285–1286; J. Amer. Chem. Soc. 105 (1983), 5665–5675).

The (thio)(thiol)phosphoric (phosphonic) ester (amide)halides III furthermore required for the synthesis of the compounds of the formula I are known from HoubenWeyl, Methoden der organischen Chemie, volume XII/2, page 274 et seq. (Stuttgart 1964), and can be prepared by the synthesis routes described there.

Some of the novel compounds of the formula I are obtained in the form of colorless or slightly brownish oils, which can be freed from the remaining volatile constituents by prolonged heating at moderately elevated temperatures under reduced pressure (incipient distillation), and purified in this manner. Where the compounds of the formula I are crystalline, they can be purified by recrystallization.

Since the compounds of the formula I generally occur as mixtures of structural isomers of the syn and anti forms, their melting or boiling ranges are not very useful for identification purposes, unless the structural isomers have been separated beforehand. Hence, in the results below, the elemental analysis and IR spectra with typical absorption maxima in the fingerprint region between 1500 cm$^{-1}$ and 900 cm$^{-1}$ are given for the particular substances prepared.

EXAMPLE 1

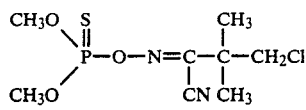

6.01 g of 2-hydroximino-3-methyl-3-(chloromethyl)-butyronitrile and 5.0 g of potassium carbonate powder are dissolved and suspended, respectively, in 40 ml of acetonitrile, and 6.35 g of O,O-dimethylthiophosphoryl chloride are added dropwise, while stirring. The mixture is stirred for 24 hours at 30° C., after which insoluble constituents are filtered off under suction and the filtrate is evaporated down under reduced pressure. The residue is taken up in methyl tert.-butyl ether, and the solution is washed once with 5% strenth sodium carbonate solution and twice with water and freed from the solvent. Incipient distillation at 70° C. and under 0.01 mbar gives 10.4 g of O-(O,O-dimethylthiophosphoryl)-2-oximino-3-methyl-3-chloromethylbutryronitrile as a virtually colorless oil. Yield: 98% of theory.

$C_8H_{14}ClN_2O_3PS$ (284.5): calculated: C 33.8, H 5.0, N 9.8, found: C 33.9, H 5.1, N 9.6.

Infrared absorptions (cm$^{-1}$): 1181, 1103, 1039, 929, 905, 870, 844.

Where one or more characteristic physical data are given, the compounds listed in the Table below have likewise been obtained in the manner described in Example 1; other compounds of the formula (I) can be obtained in the same manner with appropriate modification of the methods according to the particular amount required and, if necessary, after a preliminary experiment to determine the best reaction conditions.

TABLE

| Ex. no. | $R^1$ | $R^2$ | X | Infrared absorption (cm$^{-1}$) |
|---|---|---|---|---|
| 2 | $C_2H_5$ | $C_2H_5O$ | S | 1102, 1023, 978, 928, 901, 860, 838, 821, 800 |
| 3 | $C_2H_5$ | $CH_3$ | S | 1301, 1102, 1036, 970, 935, 911, 889 |
| 4 | $CH_3$ | $C_2H_5$ | S | 1054, 1026, 1014, 927, 893 |
| 5 | $C_2H_5$ | $C_2H_5$ | S | 1048, 1023, 1013, 927, 895, 849, 834, 809, 798 |
| 6 | $C_2H_5$ | i-$C_3H_7$—NH | O | 1469, 1438, 1258, 1167, 1046, 935, 907 |
| 7 | $C_2H_5$ | n-$C_3H_7$—S | S | 1022, 964, 922, 894, 850, 790 |
| 8 | $C_2H_5$ | sec.-$C_4H_9$—S | O | 1269, 1028, 971, 927, 924, 853, 727 |
| 9 | $CH_3$ | $CH_3O$ | O | |
| 10 | $C_2H_5$ | $C_2H_5O$ | O | 1293, 1166, 1103, 1034, 986, 936, 867 |
| 11 | $C_2H_5$ | $C_6H_5$ | S | 1123, 1034, 1026, 918, 894, 847, 793 |
| 12 | $C_2H_5$ | sec.-$C_4H_9$—S | S | 1022, 963, 923, 894, 788, 730 |
| 13 | $C_2H_5$ | n-$C_3H_7$—S | O | |

The above, and other, active ingredients according to the invention are applied in the manner usual for phosphates. Detail on formulation, application techniques and mode of action, and details of suitable mixture components for achieving synergistic and other advantageous actions are given for example in U.S. Pat. No. 4,320,122 or the publications mentioned initially, which are incorporated herein by reference.

The biological action of the active ingredients according to the invention was compared with that of the following prior art compounds:

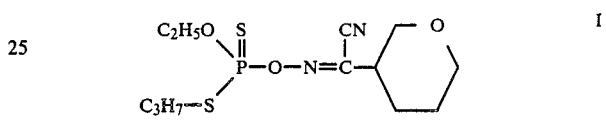

from German Laid-Open Application DE-OS No. 2,952,738

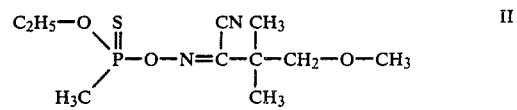

from German Laid-Open Application DE-OS No. 3,135,182 and

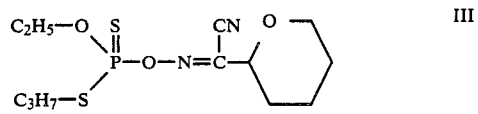

from German Laid-Open Application DE-OS No. 3,302,969.

Contact action on oriental cockroaches (*Blatta orientalis*)

The bottom of 1 liter preserving jars was lined with acetonic solutions of the candidate compounds.

After the solvent had evaporated, 5 adult cockroaches were introduced into each jar.

In this experiment, compounds 1–5 and 7 achieved, at application rate of less than 0.1 mg, the same action as comparative compounds I and II (applied at a rate 4 and 2.5 times higher, respectively).

Continuous contact action on houseflies (*Musca domestica*)

The insides of Petri dishes 10 cm in diameter were treated with acetonic solutions of the candidate compounds.

After the solvent had evaporated, 20 4-day old houseflies were placed in each dish. The kill rate was determined after 4 hours.

In this experiment, compounds 1–5 had an action at least twice as good as compound II, the most effective comparative compound.

Contact action on houseflies (Musca domestica)

1 μl of acetonic solutions of the candidate compounds was administered by means of a microsyringe to the ventral abdomen of 4-day old imagoes under slight $CO_2$ narcosis.

Cellophane bags (approx. 500 ml) were filled with 20 animals treated in this way. After 4 hours the animals in supine position were counted and the $LD_{50}$ was determined by means of a graph.

In this experiment, compounds 1–5 and 8 had an action up to 10 times better than comparative compounds I and II.

Contact action on mosquito larvae (Aedes aegypti)

Formulations of the active ingredients were added to 200 ml of tapwater; 30 to 40 mosquito larvae in the 4th larval stage were then introduced.

The temperature was kept at 20° C. The action was assessed after 24 hours.

In this experiment, compounds 1, 2 and 8 had an action which was from 2.5 to 10 times better than that of compartive agents I, II and III.

Contact action on cotton stainers (Dysdercus intermedius)

Petri dishes 10 cm in diameter were lined with 1 ml of acetonic solutions of the active ingredients.

After the solvent had evaporated, 20 larvae in the penultimate stage were placed in each dish and the action was assessed after 24 hours.

In this experiment, compounds 1 to 6 had an action up to 10 times better than that of comparative compounds I to III.

Contact action on aphids (Aphis fabae)

Potted bean plants (Vicia faba) with extensive aphid colonies were sprayed to runoff in a spray cabinet with aqueous active ingredient formulations.

Assessment took place after 24 hours.

In this experiment, compounds 1 and 2 had an action up to 10 times better than that of comparative agents I to III.

Action on caterpillars of Prodenia litura

Young Indian corn leaves were dipped for 3 seconds in aqueous active ingredient formulations. After the layers had dried, the leaves were introduced into Petri dishes 10 cm in diameter and 5 caterpillars, each about 1.5 cm long, were placed on each leaf. The action was assessed after 48 hours.

In this experiment, compounds 3 to 5 had an action at least twice as good as that of comparative agent II.

Contact action on ticks (Ornithodorus moubata)

The experiment was carried out on young ticks which had sucked blood only once. Commercially available tea-bags, each containing 5 animals, were dipped for 5 seconds in the aqueous active ingredient formulation. The bags were then suspended. The kill rate was determined after 48 hours.

In this experiment, compounds 1 to 6 had an action from 4 to 50 times (and more) stronger than that of comparative agents I to III.

Action on root-knot nematodes (Meloidogyne incognita)

30 ml of aqueous formulations of the active ingredients was intimately mixed with 300 g of mold heavily infested with Meloidogyne incognita. The mold was then filled into plastic pots and tomato seedlings were planted therein. The pots were kept under greenhouse conditions at from 22° to 24° C.

The roots were investigated for root-knots after 6 to 8 weeks.

In this experiment, compounds 4 and 5, at a concentration 2.5 to 10 times less than that of comparative agents I and II, were fully effective, whereas the comparative agents proved to be ineffective.

Intermediates

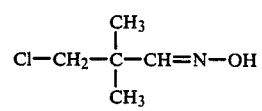

63.5 g of powdered sodium hydroxide are dissolved in a mixture of 155 ml of water and 650 ml of ethanol. While cooling, 113.5 g of hydroxylamine hydrochloride in 70 ml of water are added; the precipitated sodium chloride is filtered off and the filtrate is dripped, while stirring and at 30° C. max., into 166.5 g of chloropivalaldehyde. The reaction mixture is stirred for 12 hours at room temperature and poured into water. The aqueous phase is saturated with common salt and extracted five times, each time with 150 ml of ether. The combined extracts are dried over sodium sulfate. After removal of the solvent a yellow oil remains which is distilled under reduced pressure. There is obtained 120 g of 2-methyl-2(chloromethyl)propionaldoxime as a colorless oil with a boiling range from 63°–65° C. at 5 mbar.

Yield: 64% of theory.

Infrared absorption (cm$^{-1}$): 1382, 1367, 1296, 988, 946, 889.

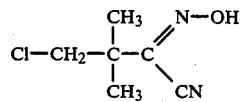

At a temperature below 0° C., 69.1 g of chlorine gas is passed into a cooled solution of 120 g of 2-methyl-2(chloromethyl)propionaldoxime in 1.2 l of ether. The volatile constituents are then removed from the reaction mixture, the residue is taken up in 600 ml of ether and the mixture is kept for 24 hours at room temperature. The liquid is then added dropwise to a suspension, cooled to 10°–15° C., of 63.4 g of potassium cyanide in 670 ml of methanol, and the whole is stirred for 3 hours at room temperature. The precipitated potassium chloride is filtered off and the residue is dissolved in methyl tert-butyl ether, washed 3 times with water and dried over magnesium sulfate. After removal of the solvent there remain 117 g of 2-hydroximino-3-methyl-3(chloromethyl)butyronitrile as a pale yellow solid, m.p. 71°–73° C.

Yield: 82% of theory.

Infrared absorption (cm$^{-1}$): 1452, 1403, 1391, 1288, 1104, 995, 938.

We claim:

1. An oximinophosphoric acid derivative

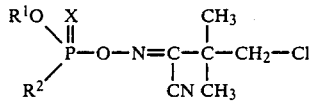 (I)

where $R^1$ is straight-chain or branched alkyl of not more than 4 carbon atoms, $R^2$ is a straight-chain or branched alkoxy or alkylthio group of not more than 4 carbon atoms, straight-chain or branched alkyl of not more than 3 carbon atoms, phenyl, amino or a straight-chain or branched alkylamino or dialkylamino radical, where alkyl in each case is of not more than 4 carbon atoms, and X is oxygen or sulfur.

2. A process for combatting pests, wherein an effective amount of an oximinophosphoric acid derivative of the formula I as set forth in claim 1 is allowed to act on pests or their habitat.

3. An oximinophosphoric acid derivative as set forth in claim 1, wherein $R^1$ is ethyl, $R^2$ is sec.butylthio and X is oxygen.

4. An oximinophosphoric acid derivative as set forth in claim 1, wherein $R^1$ is methyl, $R^2$ is ethyl and X is sulfur.

5. An oximinophosphoric acid derivative as set forth in claim 1, wherein $R^1$ is ethyl, $R^2$ is ethoxy and X is sulfur.

6. An oximinophosphoric acid derivative as set forth in claim 1, wherein $R^1$ is methyl, $R^2$ is methoxy and X is sulfur.

7. A pesticidal agent containing a solid or liquid carrier and an effective amount of at least one oximinophosphoric acid derivative of the formula I as set forth in claim 1.

* * * * *